United States Patent
El-Baz et al.

(10) Patent No.: US 10,453,569 B2
(45) Date of Patent: *Oct. 22, 2019

(54) COMPUTER AIDED DIAGNOSTIC SYSTEM FOR CLASSIFYING KIDNEYS

(71) Applicant: University of Louisville Research Foundation, Inc., Louisville, KY (US)

(72) Inventors: Ayman S. El-Baz, Louisville, KY (US); Amy Dwyer, Crestwood, KY (US); Rosemary Ouseph, Louisville, KY (US); Fahmi Khalifa, Louisville, KY (US); Ahmed Soliman, Louisville, KY (US); Mohamed Shehata, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/903,769

(22) Filed: Feb. 23, 2018

(65) Prior Publication Data

US 2018/0182482 A1 Jun. 28, 2018

Related U.S. Application Data

(63) Continuation of application No. 14/676,111, filed on Apr. 1, 2015, now Pat. No. 9,928,347.

(Continued)

(51) Int. Cl.
*G16H 30/40* (2018.01)
*A61B 5/20* (2006.01)
(Continued)

(52) U.S. Cl.
CPC ............. *G16H 30/40* (2018.01); *A61B 5/201* (2013.01); *G06F 19/321* (2013.01);
(Continued)

(58) Field of Classification Search
CPC ......... G06T 7/0012; G06T 2207/10096; G06T 2207/20081; G06T 2207/10088;
(Continued)

(56) References Cited

U.S. PATENT DOCUMENTS 9,360,488 B2 * 6/2016 Anderberg ......... G01N 33/6893
9,928,347 B2 * 3/2018 El-Baz .................. A61B 5/201
(Continued)

OTHER PUBLICATIONS

El-Baz et al., "Image analysis of renal DCE MRI for the detection of acute renal rejection." 18th International Conference on Pattern Recognition (ICPR'06). vol. 3. IEEE, 2006.*

*Primary Examiner* — Vincent Rudolph
*Assistant Examiner* — Pinalben Patel
(74) *Attorney, Agent, or Firm* — Bingham Greenebaum Doll LLP; Brian W. Chellgren

(57) ABSTRACT

A computer aided diagnostic system and automated method to classify a kidney. Image data for a medical scan that includes image data of a kidney may be received. The kidney image data may be segmented from other image data of the medical scan. One or more iso-contours may be registered for the kidney image data, and renal cortex image data may be segmented from the kidney image data based on the one or more registered iso-contours. The kidney may be classified by analyzing one or more features determined from the segmented renal cortex image data using a learned model associated with the one or more features.

17 Claims, 10 Drawing Sheets

Related U.S. Application Data

(60) Provisional application No. 61/974,134, filed on Apr. 2, 2014.

(51) Int. Cl.
| | | |
|---|---|---|
| *G06F 19/00* | (2018.01) | |
| *G06T 7/00* | (2017.01) | |
| *G06T 7/33* | (2017.01) | |
| *G06T 7/12* | (2017.01) | |
| *G06T 7/143* | (2017.01) | |
| *G16H 50/20* | (2018.01) | |
| *G16H 30/20* | (2018.01) | |

(52) U.S. Cl.
CPC .............. *G06T 7/0012* (2013.01); *G06T 7/12* (2017.01); *G06T 7/143* (2017.01); *G06T 7/33* (2017.01); *G16H 30/20* (2018.01); *G16H 50/20* (2018.01); *G06T 2207/10088* (2013.01); *G06T 2207/10096* (2013.01); *G06T 2207/20081* (2013.01); *G06T 2207/30084* (2013.01)

(58) Field of Classification Search
CPC ... G06T 2207/30084; G06T 7/33; G06T 7/12; G06T 7/143; G06F 19/321; G06F 19/345; G16H 50/20; A61B 5/20
See application file for complete search history.

(56) References Cited

U.S. PATENT DOCUMENTS

| | | | |
|---|---|---|---|
| 2005/0201601 A1* | 9/2005 | Sun | A61B 6/469 382/128 |
| 2005/0286768 A1* | 12/2005 | Battle | G06K 9/3233 382/190 |
| 2006/0013482 A1* | 1/2006 | Dawant | G06T 7/12 382/173 |
| 2008/0002870 A1* | 1/2008 | Farag | G06K 9/0014 382/128 |
| 2009/0324031 A1* | 12/2009 | Gee | G06T 7/30 382/128 |
| 2010/0081931 A1* | 4/2010 | Destrempes | G06T 7/12 600/437 |
| 2010/0111386 A1* | 5/2010 | El-Baz | G06T 7/0016 382/128 |
| 2015/0201878 A1* | 7/2015 | Chen | A61B 5/201 600/425 |

* cited by examiner

ABSTRACT
COMPUTER AIDED DIAGNOSTIC SYSTEM FOR CLASSIFYING KIDNEYS

CROSS-REFERENCE TO RELATED APPLICATION

This application is a Continuation application of U.S. application Ser. No. 14/676,111, entitled COMPUTER AIDED DIAGNOSTIC SYSTEM FOR CLASSIFYING KIDNEYS, filed Apr. 1, 2015, which application claims the benefit of Provisional Application No. 61/974,134, entitled COMPUTER AIDED DIAGNOSTIC SYSTEM FOR CLASSIFYING KIDNEYS, filed Apr. 2, 2014. The contents of each of these related Applications are hereby expressly incorporated by reference herein in their entireties.

FIELD OF THE INVENTION

The invention is generally related to computer analysis of medical image data, and in particular to the classification of kidneys using medical image data and evaluation of kidney transplant success.

BACKGROUND OF THE INVENTION

For kidney transplants, early detection of rejection is important to institute appropriate medical and immune therapy in patients. In the United States, approximately 17,000 renal transplants are performed annually, and given the limited number of donors, transplanted kidney salvage is an important medical concern. Generally, biopsy is the gold standard in the medical field for determining whether a kidney transplant is acutely rejected or not.

Therefore, a continuing need exists for non-invasive analysis of kidneys to evaluate kidney transplant success.

SUMMARY OF THE INVENTION

The invention addresses these and other problems associated with the prior art by providing a computer aided diagnostic system and automated method for classifying a kidney by analyzing image data of an abdomen scan that includes image data for the kidney. Consistent with some embodiments of the invention, image data associated with an abdomen scan that includes image data of a kidney may be received. In some embodiments of the invention, the abdomen scan may comprise dynamic contrast-enhanced magnetic resonance imaging (DCE-MRI) data, diffusion-weighted magnetic resonance imaging (DW-MRI) data, and/or other such types of image data that may be collected for medical imaging. Moreover, the abdomen scan may generally comprise a plurality of time slice images (e.g., images of a time series), such that each time slice image generally corresponds to a particular time at which the image data was captured.

Kidney image data may be segmented from other image data of the abdomen scan, and one or more iso-contours of the kidney image data may be registered. In general, registering one or more iso-contours of the kidney image data may compensate for movement of the kidney across the plurality of time slices. Based on the one or more registered iso-contours, image data for a renal cortex of the kidney may be segmented from the kidney image data. Based on the renal cortex image data, the kidney may be classified as one of an acutely rejected transplant or a non-rejected transplant by analyzing at least one feature determined from the segmented renal cortex image data using a learned model associated with the at least one feature.

These and other advantages and features, which characterize the invention, are set forth in the claims annexed hereto and forming a further part hereof. However, for a better understanding of the invention, and of the advantages and objectives attained through its use, reference should be made to the Drawings, and to the accompanying descriptive matter, in which there is described exemplary embodiments of the invention.

DETAILED DESCRIPTION

Embodiments consistent with the invention provide for automated classification of a kidney based on image analysis of at least a portion of the kidney that is in image data of a medical scan, such as an abdomen scan. Consistent with embodiments of the invention, a transplanted kidney may be classified as acutely rejected or non-rejected based at least on image analysis performed on a medical scan associated with the transplanted kidney. For example, embodiments of the invention may receive an abdomen scan that comprises a plurality of time sliced dynamic contrast-enhanced magnetic response imaging (DCE-MRI) data that includes kidney image data. Embodiments of the invention may analyze the kidney image data, and based on a learned model that classifies kidneys, the transplanted kidney may be classified based on one or more features determined from the analyzed kidney image data.

Further details are provided in [1] F. Khalifa, M. El-Ghar, B. Abdollahi, H. Frieboes, T. El-Diasty, and A. El-Baz, "A Comprehensive Non-Invasive Framework for Automated Evaluation of Acute Rental Transplant Rejection Using DCE-MRI", NMR in Biomedicine, vol. 26, issue 11, pg. 1460-1470, November 2013; [2] F. Khalifa, G. Beache, M. El-Ghar, T. El-Diasty, G. Gimel'farb, M. Kong, and A. El-Baz, "Dynamic Contrast-Enhanced MRI-Based Early Detection of Acute Renal Transplant Rejection", IEEE Transactions on Medical Imaging, vol. 32, issue 10, pg. 1910-1927, October 2013; [3] M. Shehata, F. Khalifa, A. Soliman, R. Alrefai, M. A. El-Ghar, A. Dwyer, R. Ouseph, and A. El-Baz, "A Novel Framework for Automatic Segmentation of Kidney from DW-MRI", IEEE International Symposium on Biomedical Imaging, Apr. 18, 2015; and [4] M. Shehata, F. Khalifa, A. Soliman, M. A. El-Ghar, A. Dwyer, R. Ouseph, and A. El-Baz, "4D Diffusion MRI-Based CAD System for Early Diagnosis of Acute Renal Rejection", MICCAI 2015, Berlin, Germany, October 2015, all of which are incorporated by reference in their entirety, and thus form a part of the instant disclosure.

Figure 1:
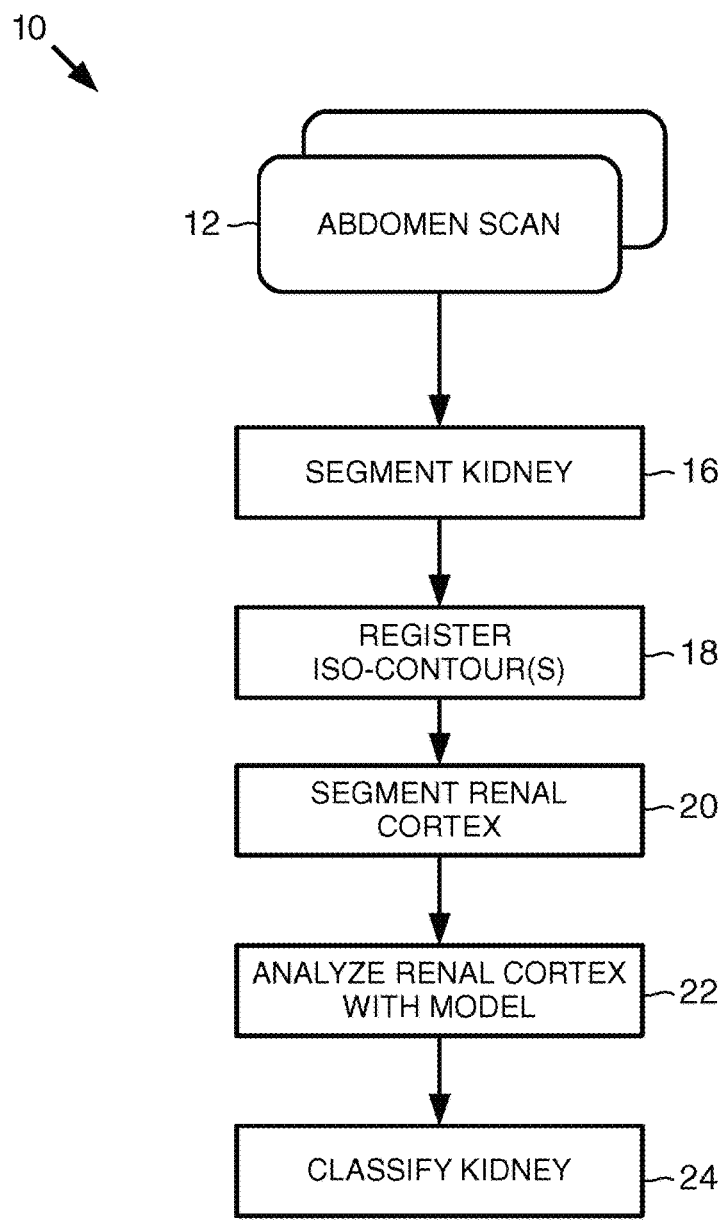
FIG. 1 is a flowchart of an automated kidney classification process.

Now turning to the Drawings, wherein like numbers denote like parts throughout the several views, FIG. 1 illustrates an exemplary automated process 10 classification of a kidney. Process 10 in particular is based upon the determination/classification of a transplanted kidney as acutely rejected or non-rejected. Process 10 receives as input one or more abdomen scans, and begins by segmenting kidney image data from the other image data of the one or more abdomen scans (block 16). In general, an abdomen scan may include one or more two dimensional "slices" of image data generated from a medical imaging device such as a CT scanner, an MRI imager, or other medical imaging device.

Once the kidney image data is segmented, one or more iso-contours may be used to register the kidney image data (block 18). In general, because a medical image scan may include a plurality of time sliced images, motion effects may be compensated for between the image frames of the plurality of time slices to thereby facilitate analysis of corresponding features across the time series. Therefore, consistent with embodiments of the invention, one or more iso-contours may be registered such that perfusion-related features are accurately identified and analyzed across the time series. Consistent with embodiments of the invention, the one or more iso-contours of the kidney image data may be registered based on geometric features of the kidney image data. For example, the one or more iso-contours of the kidney image data may be registered by using a Laplace partial differential equation to determine point-to-point correspondences between kidney objects to identify and register iso-contours across the time series of the kidney image data. Based on the registered kidney objects, renal cortex image data may be segmented from the kidney image data (block 20).

Following cortex segmentation, embodiments of the invention may determine one or more features associated with the kidney based on the renal cortex image data. Based on the one or more features, the renal cortex may be analyzed with one or more learned models associated with the one or more features (block 22). Generally, a learned model may be developed based on known training sets of classified transplanted kidneys and based on the one or more features determined for such classified transplanted kidneys.

In some embodiments of the invention, perfusion values may be a feature that may be determined based on the renal cortex image data. For example, perfusion values for a transplanted kidney may be determined based at least in part on signal intensity versus time curves for at least a portion of the kidney image data, including for example, at least a portion of the renal cortex image data. Moreover, to compensate for various other physiological characteristics of patients, some embodiments of the invention may normalize the one or more determined features based at least in part on a corresponding feature for a segment of image data not associated with the kidney, such as a segment of image data corresponding to a body wall muscle proximate the kidney.

After analyzing the renal cortex image data with the learned model, including for example, analyzing the one or more determined features with the learned model, embodiments of the invention may classify the kidney associated with the received abdominal scan (block 24). Therefore, consistent with some embodiments of the invention, a kidney may be classified and/or evaluated. In particular, in some embodiments, a transplanted kidney may be classified as acutely rejected or non-rejected—i.e., the success of a kidney transplant may be evaluated.

Figure 2:
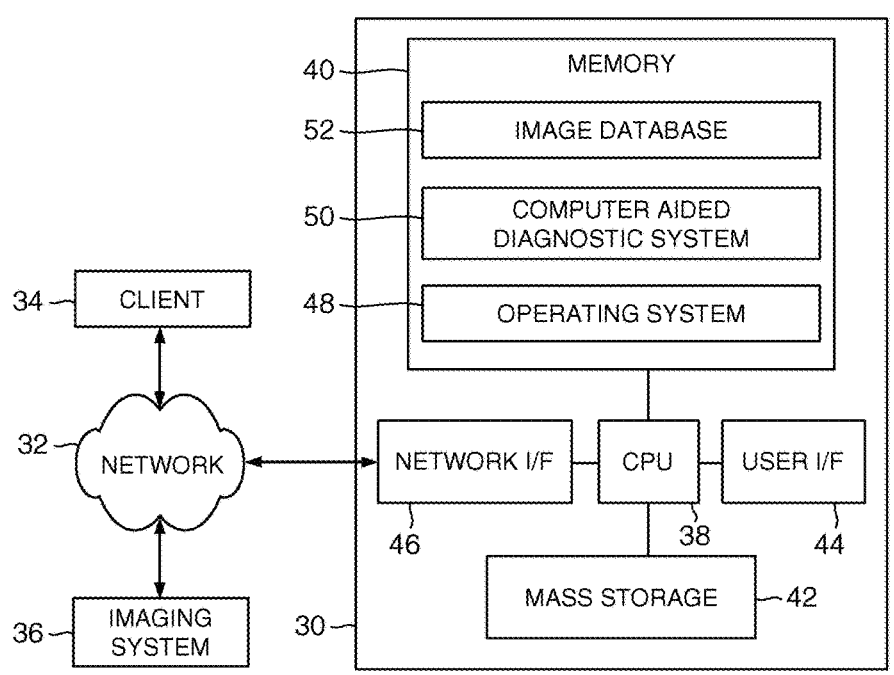
FIG. 2 is a block diagram of an exemplary apparatus suitable for implementing steps from the process of FIG. 1.

One or more steps in process 10 may be implemented in an automated fashion, utilizing a computer or other electronic device to implement such steps. FIG. 2, for example, illustrates an exemplary apparatus 30 within which various steps from process 10 may be implemented in a manner consistent with the invention. Apparatus 30 in the illustrated embodiment is implemented as a server or multi-user computer that is coupled via a network 32 to one or more client computers 34, as well as an imaging system 36, e.g., a two dimensional dynamic contrast-enhanced magnetic resonance imaging device, a helical or multi-slice LDCT scanner, etc. For the purposes of the invention, each computer 30, 34 may represent practically any type of computer, computer system, data processing system or other programmable electronic device. Moreover, each computer 30, 34 may be implemented using one or more networked computers, e.g., in a cluster or other distributed computing system. In the alternative, computer 30 may be implemented within a single computer or other programmable electronic device, e.g., a desktop computer, a laptop computer, a handheld computer, a cell phone, a set top box, etc.

Computer 30 typically includes a central processing unit 38 including at least one microprocessor coupled to a memory 40, which may represent the random access memory (RAM) devices comprising the main storage of computer 30, as well as any supplemental levels of memory, e.g., cache memories, non-volatile or backup memories (e.g., programmable or flash memories), read-only memories, etc. In addition, memory 40 may be considered to include memory storage physically located elsewhere in computer 30, e.g., any cache memory in a processor in CPU 38, as well as any storage capacity used as a virtual memory, e.g., as stored on a mass storage device 42 or on another computer coupled to computer 30. Computer 30 also typically receives a number of inputs and outputs for communicating information externally. For interface with a user or operator, computer 30 typically includes a user interface 44 incorporating one or more user input devices (e.g., a keyboard, a mouse, a trackball, a joystick, a touchpad, and/or a microphone, among others) and a display (e.g., a CRT monitor, an LCD display panel, and/or a speaker, among others). Otherwise, user input may be received via another computer or terminal.

For additional storage, computer 30 may also include one or more mass storage devices 42, e.g., a floppy or other removable disk drive, a hard disk drive, a direct access storage device (DASD), an optical drive (e.g., a CD drive, a DVD drive, etc.), and/or a tape drive, among others. Furthermore, computer 30 may include an interface 46 with one or more networks 32 (e.g., a LAN, a WAN, a wireless network, and/or the Internet, among others) to permit the communication of information with other computers and electronic devices. It should be appreciated that computer 30 typically includes suitable analog and/or digital interfaces between CPU 36 and each of components 40, 42, 44 and 46 as is well known in the art. Other hardware environments are contemplated within the context of the invention.

Computer 30 operates under the control of an operating system 48 and executes or otherwise relies upon various computer software applications, components, programs, objects, modules, data structures, etc., as will be described in greater detail below. Moreover, various applications, components, programs, objects, modules, etc. may also execute on one or more processors in another computer coupled to computer 30 via network 32, e.g., in a distributed or client-server computing environment, whereby the processing required to implement the functions of a computer program may be allocated to multiple computers over a network.

As an example, computer 30 may include a computer aided diagnostic (CAD) system program 50 used to implement one or more of the steps described above in connection with process 10. For the purposes of implementing such steps, an image database 52, storing medical image scans, may be implemented in computer 30. It will be appreciated, however, that some steps in process 10 may be performed manually and with or without the use of computer 30.

In general, dynamic magnetic resonance imaging time series (i.e., DCE-MRI image data) may be subject to relatively low signal-to-noise, non-uniform intensity distribution over a time series of the image data, which may be due to respiratory and physiological motion. Hence, accurate segmentation of image data for a kidney may be challenging. Embodiments of the invention may generate deformable prototypes with level sets that may provide flexible evolution on an xy-plane with no need for parameterization. A level set function ø may correspond to a distance map of signed minimal Euclidian distances from every point (x, y) of the plane to the boundary (negative for interior points and positive for exterior points). Generally, the level set function evolves in the discrete time-space domain according to the following equation:

$$\phi_{n+1}(x,y) = \phi_n(x,y) - \tau F_n(x,y) |\nabla \phi_n(x,y)|, \quad (1)$$

where n is a discrete instant of time t=nτ taken with a step τ>0, $F_n(x,y)$ is a speed function controlling evolution, and $$\nabla \phi_n(x, y) = \left[ \frac{\partial \phi_n}{\partial x}, \frac{\partial \phi_n}{\partial y} \right]$$

corresponds to a gradient of $\phi_n(x,y)$.

For segmentation of image data, embodiments may implement a stochastic speed function that may depend on at least three features: a weighted probabilistic shape prior, pixel-wise image intensities, and high-order spatial interactions. The features may be integrated into a joint, bi-level, probabilistic Markov-Gibbs random field (MGRF) model of the kidney and its background. A probabilistic MGRF model of the kidney and background may be described by the following equations:

$$R = \{(x,y): 0 \leq x \leq X-1, 0 \leq y \leq Y-1\}, \quad (2)$$

where R denotes a finite arithmetic lattice of the size XY supporting grayscale images and their region (segmentation) maps;

$$Q = \{0,1,\ldots,Q-1\} \quad (3)$$

denotes a finite set of $Q$ integer gray values;

$$L = \{0,1\}, \quad (4)$$

denotes a binary set of object ("1") and background ("0") labels;

$$g = \{g_{x,y}: (x,y) \in R; g_{x,y} \in Q\} \quad (5)$$

is a grayscale image taking values from $Q$ (i.e., g:R→$Q$); and $$m = \{m_{x,y}: (x,y) \in R; m_{x,y} \in L\} \quad (6)$$

is a region map taking values from L (i.e., m:R→L).

An input image g of the image data may be co-aligned to a shape prior model, and a region map m of the input image may be described with a joint probability model provided by the following equation:

$$P(g,m) = P(g|m)P(m), \quad (7)$$

where P(g|m) is a conditional distribution of the images given the map;

$$P(m) = P_s(m)P_V(m) \quad (8)$$

is an unconditional probability distribution of maps;
  $P_s(m)$ denotes a weighted shape prior model, and
  $P_V(m)$ is a Gibbs probability distribution with potentials V, which specifies a MGRF model of spatially homogenous maps m.

Figure 3:
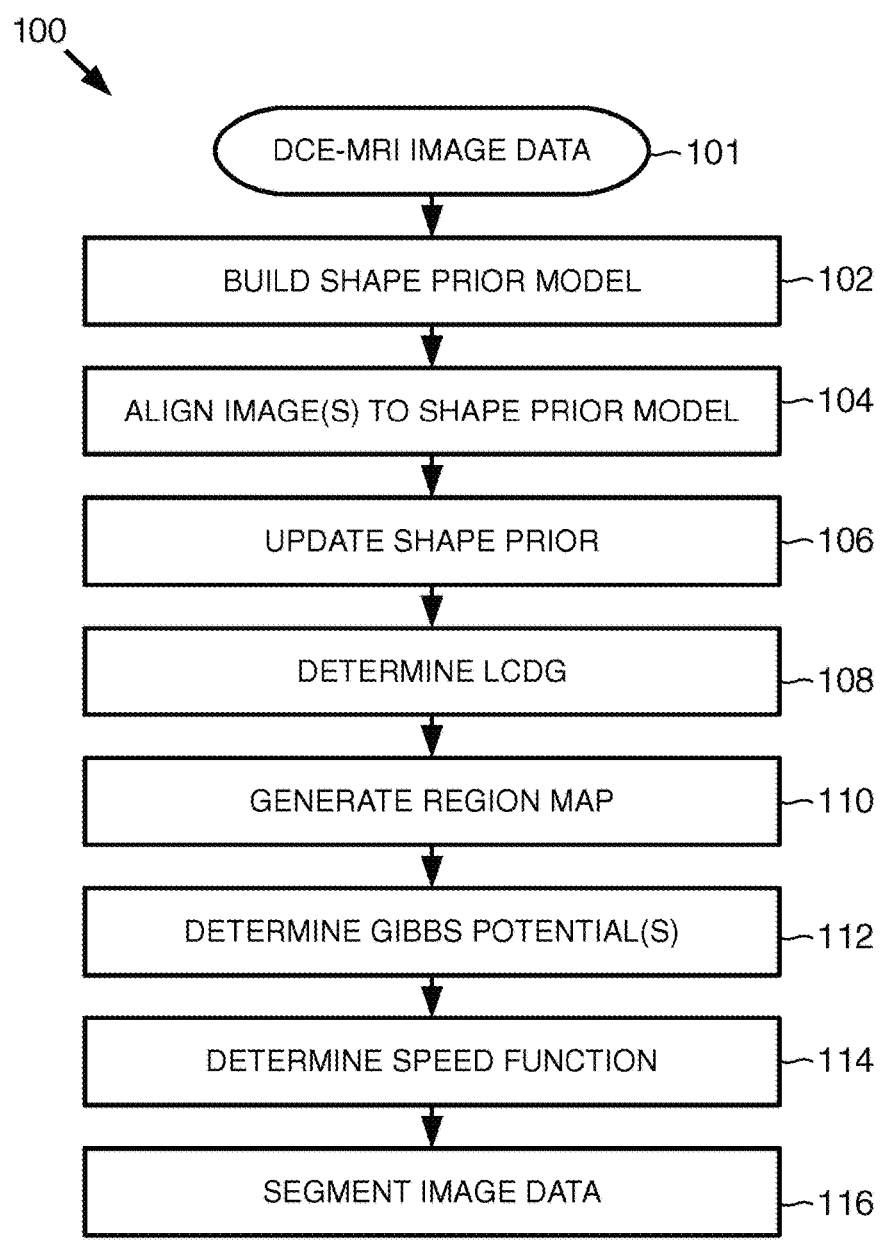
FIG. 3 is a flowchart that illustrates a sequence of operations that may be performed by the computer of FIG. 2.

FIG. 3 provides a flowchart 100 that illustrates a sequence of operations that may be performed by the computer 30 to segment each image received in image data 101 for one or more DCE-MRI scans consistent with embodiments of the invention. As shown, the computer 30 may build a shape prior model that is based on training sets of image data of kidneys (block 102). Generally, embodiments of the invention may implement a level set evolution using an adaptive shape prior of the kidney that may be built for a set of training images, which may be collected from different subjects. Variability of shapes may be reduced to obtain more accurate segmentation by mutually co-aligning training images with a two-dimensional affine transformation, which generally maximizes mutual information for the training images. A shape prior model may be generated based at least in part on training images in which kidney borders have been identified, where the training images may specify region maps for co-aligned training images. A shape prior model may be generated as a spatially variant independent random field of region labels in the following maps:

$$P_s(m) = \Pi_{(x,y) \in R} \, p_{s:x,y}(m_{x,y}), \quad (9)$$

where $p_{s:x,y}(1)$, and $p_{s:x,y}(0) = 1 - p_{s:x,y}(1)$, and correspond to the empirical pixel-wise probabilities of kidney and background.

The computer 30 may align images of the image data to the shape prior model (block 104). Each input image of image data to be segmented may be co-aligned to at least one training image. The computer 30 may update the shape prior based at least in part on the co-aligned images and the shape prior model (block 106). Consistent with embodiments of the invention, normalized cross-correlation (NCC) values (i.e., $\eta_j$; j=1, ..., N) between the co-aligned input image and each of the N training images may be determined. A weighted sum of the training region maps may be computed for the aligned images, and the shape prior model may be updated based at least in part on the weighted sums. A pixel-wise kidney probability (i.e., $p_{s:x,y}(1)$) may be determined based at least in part on a weighted sum of occurrences of the pixel (x, y) in the kidney region in all training maps based at least in part on the following equation:

$$p_{s:x,y}(1) = \frac{1}{\alpha}\sum_{J=1}^{N}\eta_j m_{j:x,y}, \text{ where } \alpha = \sum_{j=1}^{N}\eta_j. \quad (10)$$

Based on the aligned images the updated shape prior model, the computer 30 determines a linear combination of discrete Gaussians (LCDG) (block 108). In general, to account for inhomogeneity of a kidney (e.g., cortex and medulla), high-order pair-wise spatial interactions between region labels of a map m may be added. Particularly, triple and quad cliques may be added. If $C_a$ denotes a family of s-order cliques of an interaction graph with nodes in the lattice sites (x, y) and edges connecting the interacting, or interdependent, sites, large variations of DCE-MRI based image data related to transit of contrast agent, label interactions may be modeled by a spatially homogenous MGRF with up to fourth-order interactions over a nearest eight neighborhood of pixels based on the following equation:

$$P_V(m) = \left(\frac{1}{Z_V}\right)^{\left(\sum_{a=1}^{A}\Sigma_{C\in c_a} V_a(m(x,y):(x,y)\in c)\right)}, \quad (11)$$

where A clique families describe the geometry of interactions;
$V=[V_a:\{0,1\}\rightarrow(-\infty,\infty): a=1, \ldots, A]$ is a collection of Gibbs potential functions $V_a$ for the families $C_a$, and the partition function $Z_V$ normalizes the probabilities over the parent population $\mathbb{M}=\{0,1\}^{XY}$ of all the maps.

Based on the LCDGs, the computer 30 may determine a region map that identifies pixels corresponding to the kidney and pixels corresponding to background (block 110). In general, an initial region map m may be determined by pixel-wise classification, and such initial region map may facilitate determination of maximum likelihoods of potentials and determination of pixel-wise probabilities of region labels at each step of a contour evolution. Consistent with some embodiments, equality or inequality of labels may be evaluated for a clique c, such that corresponding second-order potentials may correspond to the following equations:

$$V_a(m(x_1,y_1),m(x_2,y_2))=V_{2:a:eq} \quad (12)$$

if $m(x_1,y_1)=m(x_2,y_2)$, otherwise $V_a(m(x_1,y_1),m(x_2,y_2))=-V_{2:a:eq}$.

Third-order potentials may correspond to the following equation:

$$V_a(m(x_1,y_1),m(x_2,y_2),m(x_3,y_3))=V_{3:a:eq_3} \quad (13)$$

if $m(x_1,y_1)=m(x_2,y_2)=m(x_3,y_3)$,
otherwise $V_a(m(x_1,y_1),m(x_2,y_2),m(x_3,y_3))=-V_{3:a:eq_3}$.

Fourth-order potentials may correspond to the following equation:

$$V_a(m(x_1,y_1),m(x_2,y_2),m(x_3,y_3),m(x_4,y_4))=V_{4:a:eq_j} \quad (14)$$

if there are j=4 or j=3 equal labels, otherwise $$V_a(m(x_1,y_1),m(x_2,y_2),m(x_3,y_3),m(x_4,y_4))=-(V_{4:a:eq_3}+V_{4:a:eq_4}).$$

The computer may determine Gibbs potentials for the fourth-order MGRF model of the region map m (block 112).

The determined Gibbs potentials from a given map m, i.e., the determination of the values $V_{2:a:eq}$, $V_{3:a:eq_3}$, $V_{4:a:eq_3}$, and $V_{4:a:eq_4}$ may be implemented to extend second-order MGRF models to higher-order MGRF models.

A visual appearance of a kidney region and surrounding tissue (i.e., background) in an image may be modeled by separating a mixed empirical marginal one dimensional distribution of pixel intensities into two individual components corresponding to a dominant kidney and background modes. The empirical distribution may be approximated with a linear combination of LCDG and automatically separated into kidney and its background components to form LCDG models. Additional details regarding the determination of Gibbs potentials may be found, for example, in the incorporated description material [2].

LCDG models may be determined based at least in part on the following equation:

$$\Psi_\theta=(\psi(q|\theta):q\in Q) \quad (15)$$

denotes a discrete Gaussian with parameters $\theta=(\mu,\sigma)$.

A continuous one-dimensional Gaussian density with the mean $\mu$ and the variance $\sigma^2$ may be integrated over successive gray level intervals. A particular LCDG with two dominant positive discrete Gaussians and $C_p \geq 2$ positive and $C_n \geq 0$ negative subordinate discrete Gaussians may be defined by the following equation:

$$P_{w,\Theta}(q)=\Sigma_{k=1}^{C_p}\omega_{pK:k}\omega(q|\theta_{p:k})-(q|\theta_{p:k}), \quad (16)$$

where weights $w=[w_{p:k}, w_{n:k}]$ are non-negative and meet an obvious constraint $\Sigma_{k=1}^{C_p} w_{p:k} - \Sigma_{k=1}^{C_n} w_{n:k} = 1$.

All LCDG parameters, including a number of discrete Gaussians, may be determined from a mixed empirical distribution to be modeled. The distribution and its components may be modeled with LCDGs more accurately that with a model including only positive discrete Gaussians or other such unimodal distributions associated with each component.

With the weighted probabilistic shape prior, pixel-wise image intensities, and higher-order spatial interaction terms, embodiments of the invention may facilitate pixel-wise guidance of the level set. In general, $p(q|l)$ denotes the pixel-wise probability of the intensity $q\in Q$ of the LCDG model of a kidney ($l=1$) or background ($l=0$) appearance, and $p_{V:x,y}(1)$ corresponds to the probability of the kidney label for the pixel (x, y) of the region map m in the MGRF model $P_V(m)$ at the current evolution step. The computer may analyze the Gibbs potentials of the MGRF model based at least in part on the following equations:

Let $$P_{1:x,y}=\frac{\Omega_{1:x,y}}{\Omega_{1:x,y}+\Omega_{0:x,y}} \text{ and } P_{0:x,y}=\frac{\Omega_{1:x,y}}{\Omega_{1:x,y}+\Omega_{0:x,y}}=1-P_{1:x,y},$$

where $\Omega_{1:x,y}=p(q|1)p_{V:x,y}(1)p_{s:x,y}(1)$, and
$\Omega_{0:x,y}=p(q|0)(1-p_{V:x,y}(1))(1-p_{s:x,y}(1))$ Then, the speed function of equation (1) may be defined as the following equation:

$$F(x,y)=\kappa\vartheta(x,y), \quad (18)$$

where $\kappa$ corresponds to a mean contour curvature and $\vartheta(x,y)$ corresponds to a magnitude and direction of contour evolution at the point (x, y), and $$\stackrel{.}{\wp}(x, y) = \begin{cases} -P_{1:x,y} & \text{if } P_{1:x,y} > P_{0:x,y} \\ P_{0:x,y} & \text{otherwise} \end{cases}.$$

The computer determines a speed function (block 114) for the image data, where the speed function may be used to compensate for motion over a time series of images of the image data. The computer 30 segments the image data (block 116) by evolving the level set function ø guided by the speed function. As will be appreciated, the segmented image data comprises image data of each image determined to correspond to a kidney based on the process described above such that image data corresponding to background is removed.

Figure 4A:
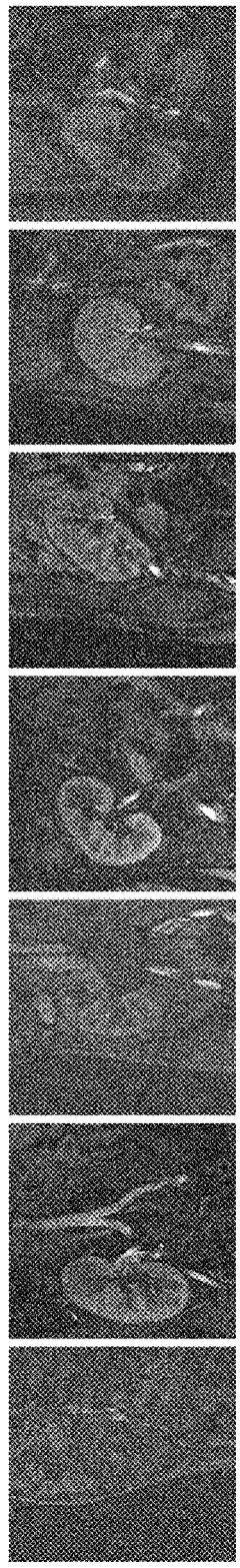
FIGS. 4A-C provide diagrammatic illustrations of kidney image data and segmented kidney image data that may be processed by the computer of FIG. 2 to build a kidney shape prior model.
Figure 4B:
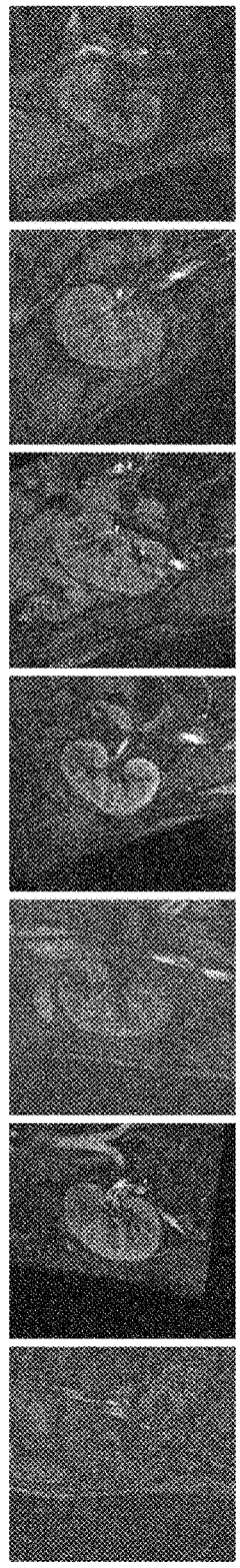
Figure 4C:
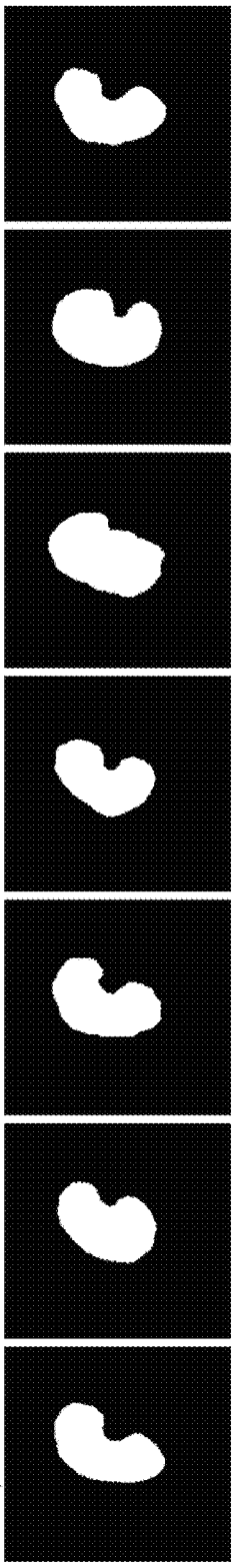
Figure 5:
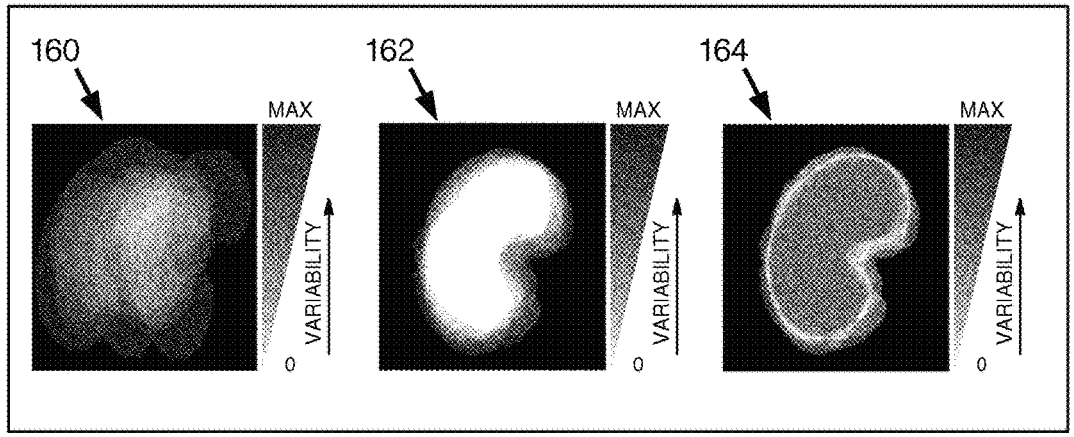
FIG. 5 provides a diagrammatic illustration of kidney shape prior image data that may be processed by the computer of FIG. 2.
Figure 6:
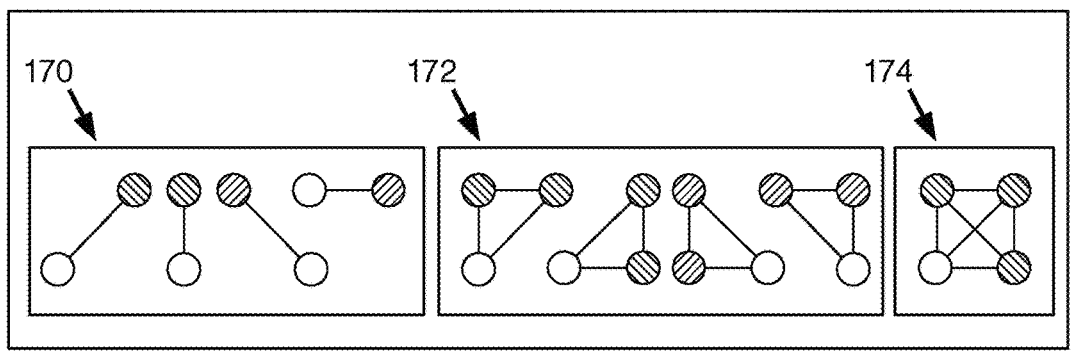
FIG. 6 provides a diagrammatic illustration of example pixel-wise neighborhoods that may be implemented by the computer of FIG. 2 to process image data.

FIGS. 4A-C provide diagrammatic illustrations of image data including images of kidneys that may be segmented consistent with some embodiments. FIG. 4A provides example images of kidneys 150 that may be received as image data consistent with some embodiments of the invention. FIG. 4B illustrates an example affine based alignment data 152 of the images 150 of FIG. 4A. FIG. 4C illustrates example segmented image data 154 that may be determined from the images 150 of FIG. 4A. As will be appreciated, in some embodiments, the images of kidneys 150, the aligned data 152, and the segmented image data 154 may be used to generate a shape prior model. FIG. 5 illustrates example images of kidneys 160 prior to alignment, after affine based registration 162, and a grayscale visualization of a shape prior model 164 generated by analysis and alignment of the example images of kidneys 160. FIG. 6 provides a diagrammatic illustration that illustrates example second-order cliques 170, third-order cliques 172, and fourth-order cliques 174 for a nearest 8-pixel neighborhood.

After affine registration and kidney segmentation, non-rigid registration may be performed to compensate for local kidney motion and/or deformations over a time of the image acquisition for the images of the image data. Consistent with some embodiments of the invention, geometric features of the segmented image data may be used to perform registration of the segmented image data, which may overcome problems associated with intensity variations associated with the temporal dynamic contrast data set of DCE-MRI image data. Solutions for a Laplace partial differential equation may facilitate determining point-to-point correspondences between nested equi-spaced iso-contours in target and reference segmented image data and kidney objects of the segmented image data.

Figure 7:
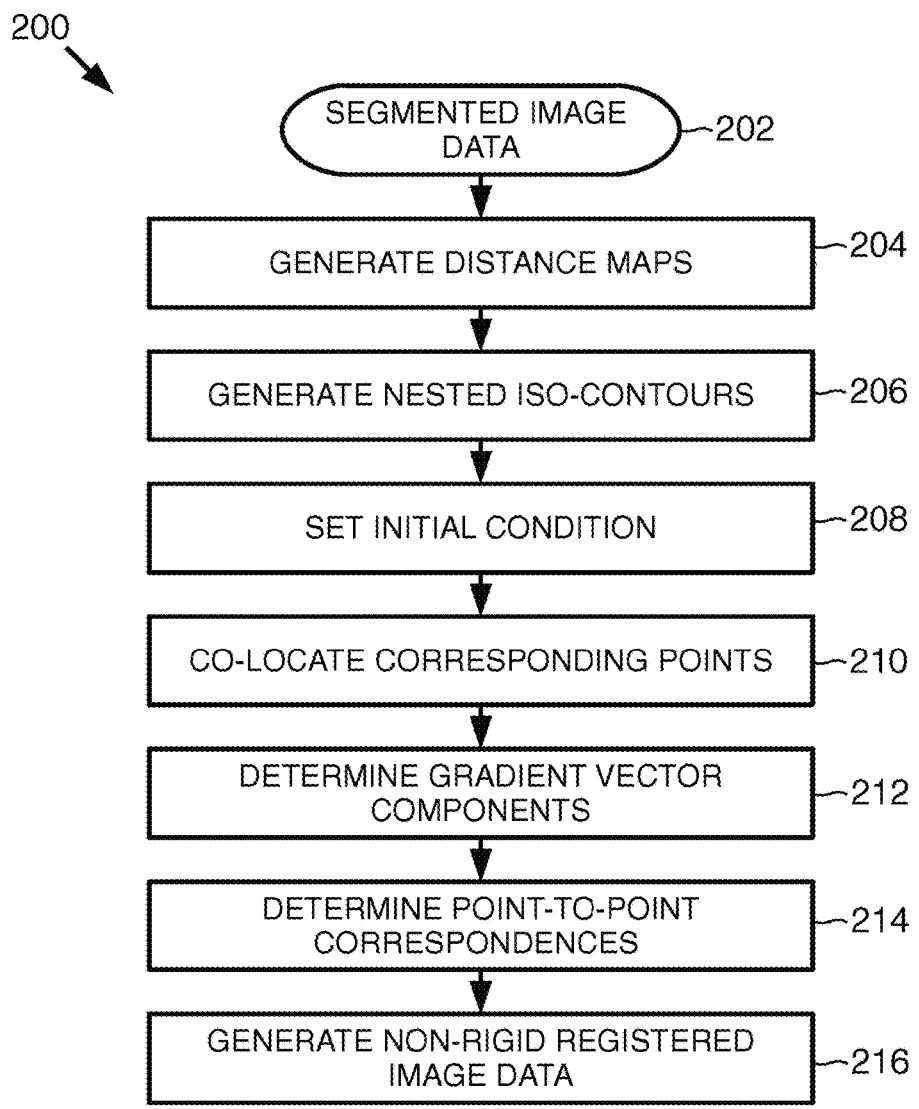
FIG. 7 is a flowchart that illustrates a sequence of operations that may be performed by the computer of FIG. 2.

FIG. 7 provides a flowchart 200 that illustrates sequence of operations that may be performed by the computer 30 to thereby perform iso-contours based nonrigid registration for segmented image data 202 consistent with embodiments of the invention. The computer 30 may analyze the segmented image data to generate distance maps (block 204), where a distance map may be generated inside a binary object area by finding a minimum Euclidean distance for every inner point to an object boundary. External points may be excluded from analysis. A Laplace equation may be applied to a reference iso-contour and a target iso-contour to co-locate corresponding points therebetween. A second order linear partial differential equation (PDE) may be implemented for determining point-to-point correspondences, as defined in the following equation:

$$\nabla^2 \gamma = \frac{\partial^2 \gamma}{\partial x^2} + \frac{\partial^2 \gamma}{\partial y^2} = 0, \quad (19)$$

where γ defines a scalar field, called a harmonic function.

Figure 8:
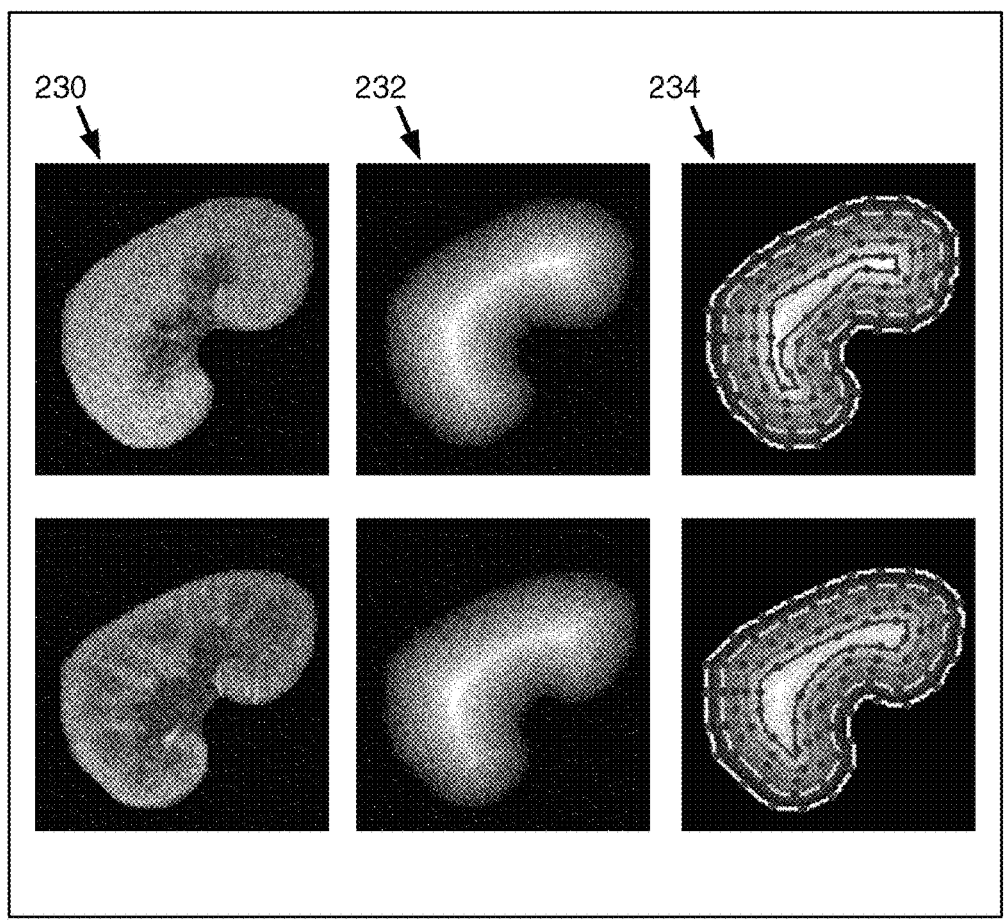
FIG. 8 provides a diagrammatic illustration of example image data and iso-contours that may be processed by the computer of FIG. 2.
Figure 9:
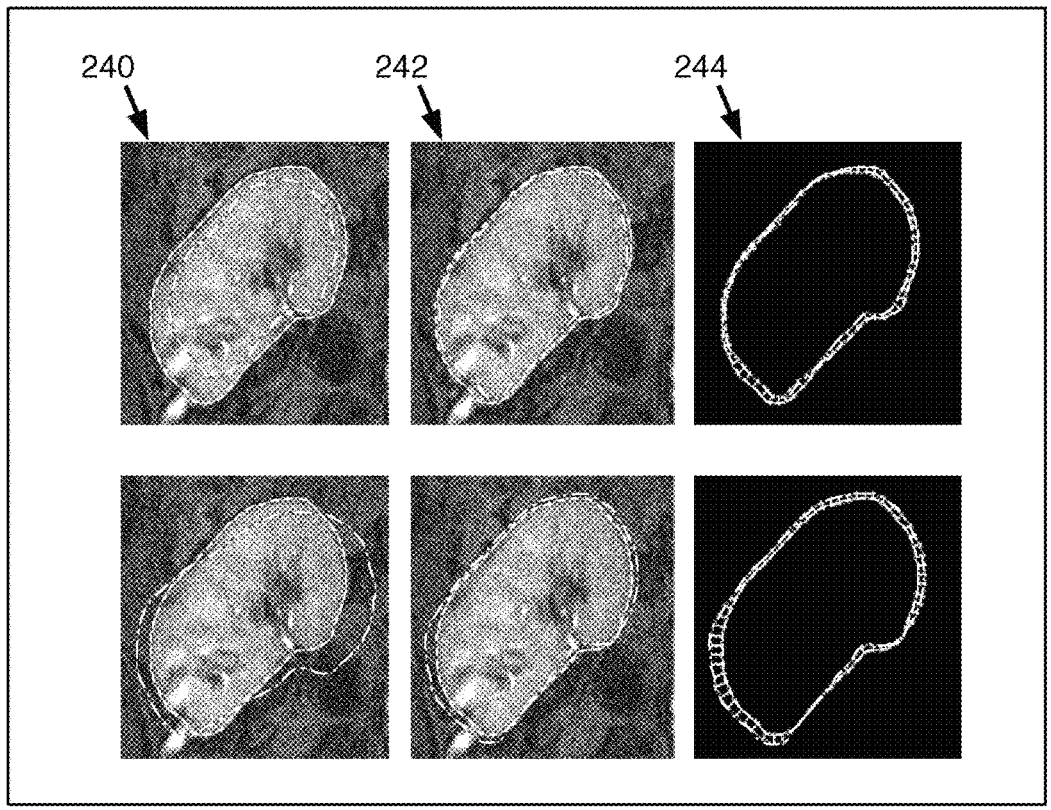
FIG. 9 provides a diagrammatic illustration of example image data and point-to-point correspondences that may be processed by the computer of FIG. 2.

The computer 30 generates nested iso-contours for a target and reference map for the segmented image data (block 206), and the computer 30 sets an initial condition (block 208) by setting a maximum and minimum (zero) potential y at the target iso-contour and corresponding reference iso-contour. Based on the initial condition, the computer co-locates corresponding points between the reference and target iso-contours (block 210) by solving equation (19) using the initial condition. Gradient vector components $$E_x = \frac{\partial \gamma}{\partial x} \text{ and } E_y = \frac{\partial \gamma}{\partial y}$$

may be determined (block 212), and the computer 30 may determine point-to-point correspondences (block 214) between the reference and target iso-contours that may be matched by forming streamlines based on the gradient vector components. Based on the point-to-point correspondences, the computer generates nonrigid registered image data such that iso-contours of segmented image data of a kidney across a time series are registered (block 216). FIG. 8 provides a diagrammatic illustration of example iso-contours that may be generated consistent with embodiments of the invention. As shown, reference and target images 230 may be used to determine distance maps 232, which may be used to generate iso-contours 234 for the segmented image data for performing nonrigid registration. FIG. 9 provides a diagrammatic illustration of co-location of point-to-point correspondences for two possible scenarios of kidney mis-registration. As shown, a reference iso-contour (illustrated in dashed line) and a target iso-contour (illustrated as a solid line) may be misaligned prior to affine alignment 240. After affine alignment 242, streamlines (illustrated as lines joining the reference iso-contour and target iso-contour) 244 may be determined based on the Laplace equation as described above.

Figure 10:
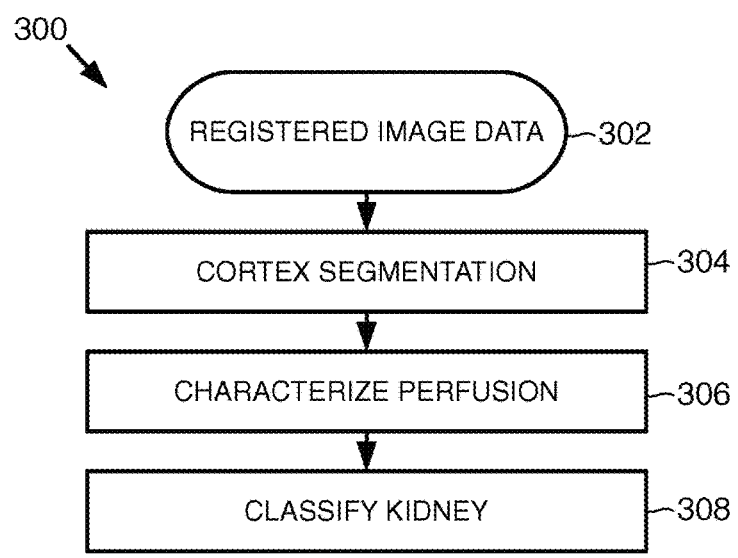
FIG. 10 is a flowchart that illustrates a sequence of operations that may be performed by the computer of FIG. 2.

FIG. 10 provides a flowchart 300 that illustrates a sequence of operations that may be performed by the computer 30 to classify a kidney for which image data has been collected, segmented, and registered. As shown, registered image data 302 may be segmented such that image data corresponding to a cortex of the kidney is determined (block 304). In general, vascular insults directly affect the kidney cortex. Hence, the cortex of the co-aligned kidneys may be segmented after the nonrigid registration. To segment the cortex, the deformable model may be applied again, using only intensity and spatial features to guide the evolution. Since the images are co-registered, the deformable boundary evolves with respect to a circular contour initialized at the center of the registered kidney. After the cortex is segmented, the image data corresponding to the cortex may serve as a mask propagating over the remaining co-registered image frames of a given perfusion time series.

The computer may characterize perfusion for the kidney using the image data corresponding to the cortex (block 306). Following the cortex segmentation, agent kinetic curves (signal intensity versus time curves) may be constructed by estimating average intensities over the entire cortex for each image frame of the time series. In general, characterization of perfusion may comprise generating a time intensity curve (TIC) by calculating the average intensities of the cortex over the time series.

To control for different physiological factors at different patient imaging exams, the computer may normalize perfusion values obtained for the cortex by the perfusion of an adjacent segment of body wall muscle that was obtainable for each subject (i.e., patient). Furthermore, embodiments may also characterize agent delivery (i.e., perfusion) during a more slowly varying phase (e.g., plateau, or tissue distribution phase), starting at approximately 30 seconds and effectively extending to approximately two minutes for peripheral injections. As will be appreciated, the characterization performed during the slowly varying phase may incorporate a large number of data points over the signal intensity time series to characterize perfusion.

Based on the perfusion characterization, the computer may classify the kidney (block 308). To distinguish between the non-rejection and acute rejection cases, the computer 30 may implement a $k_n$-nearest neighbor classifier to analyze statistical characteristics of perfusion curves averaged over the entire cortex. The characteristics may be determined from training sets of image data for kidneys including both non-rejection and acute rejection cases. In some embodiments, four perfusion indexes may be used to classify the test cases. In addition, in some embodiments, the $k_n$ classifier may be augmented by analyzing all four indexes with weights, determined by genetic optimization corresponding to the training data sets. The weights may be determined by maximizing a Euclidean distance between the weighted-combined indexes of the non-rejection and acute rejection groups in order to better classify the training data, based on a biopsy ground truth.

Figure 11:
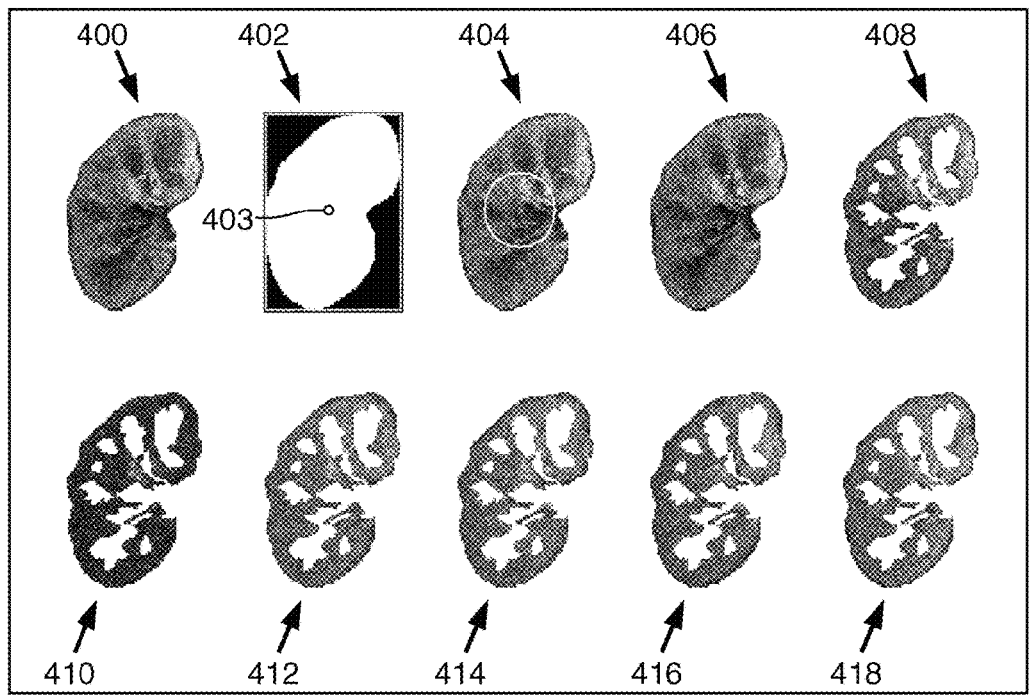
FIG. 11 provides a diagrammatic illustration of image data, a cortex mask, and application of the cortex mask to segment renal cortex image data that may be processed by the computer of FIG. 2.

The computer may classify a kidney corresponding to the received image data based at least in part on the perfusion characterization and/or time intensity curve. FIG. 11 provides a diagrammatic illustration of processing of image data consistent with embodiments of the invention. In this example, a kidney image 400 after nonrigid alignment is shown; a bounding box 402 is determined that yields a seed point 403 that may be used for level set initialization; an initial boundary 404 of the kidney object is based on the seed point 403; a final kidney boundary 406 may be determined that corresponds to a cortex of the kidney object; an extracted cortex mask 408 may be determined and may be applied to time series images corresponding to the kidney object 400 to segment image data from the time series images corresponding to the cortex 410-418.

Figure 12:
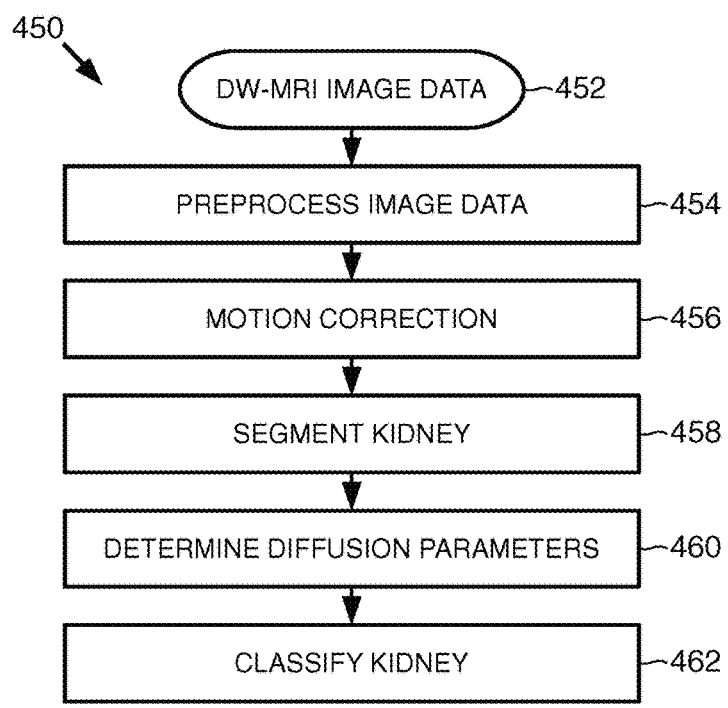
FIG. 12 is a flowchart that illustrates a sequence of operations for diffusion weighted magnetic resonance imaging data that may be performed by the computer of FIG. 2.

Consistent with some embodiments, the image data received by the computer 30 may comprise four-dimensional DW-MRI data that generally includes three-dimensional data and a b-value (which corresponds to a strength and direction of a magnetic diffusion gradient). In these embodiments, an image of a time series may comprise a voxel (i.e., an image data point having three dimensions). FIG. 12 provides a flowchart 450 that illustrates a sequence of operations that may be performed by the computer 30 to process DW-MRI image data 452 consistent with embodiments of the invention. The computer 30 preprocesses the image data 452 (block 454) by applying intensity histogram equalization using a nonparametric bias correction process to the image data. In general, the computer 30 may preprocess the image data to compensate for low frequency intensity non-uniformity or inhomogeneity. The computer 30 performs motion correction on the image data (block 456) by performing a three-dimensional B-splines transformation using a sum of square difference as a similarity metric.

A kidney object may be segmented from the image data (block 458). Consistent with embodiments of the invention, the computer 30 may integrate regional statistics derived from kidney and background regions may be used to determine portions of the image data corresponding to the kidney object and portions of the image data corresponding to background. Embodiments of the invention may analyze appearance, shape, and/or spatial features of the image data using a joint MGRF image model. As will be appreciated, in these embodiments, the image data comprises three-dimensional data and further includes b-value data. Therefore, a joint MGRF image model may be constructed based at least in part on the following equations:

$$R=\{(x,y):0\le x\le X-1, 0\le y\le Y-1, 0\le z\le Z-1\}, \quad (20)$$

$Q=\{0, 1, Q-1\}$; and $L=\{0, 1\}$, where L denotes a finite 3D arithmetic lattice supporting grayscale images and their region (segmentation) maps, a finite set of $Q$ integer gray values, and a binary set of region labels, i.e., object ("1") and background ("0") labels.

$g=\{g_{x,y,z}:(x,y,z)\in R; g_{x,y,z}\in Q\}$,
$m=\{m_{x,y,z}:(x,y,z)\in R; m_{x,y,z}\in L\}$ is a grayscale image taking values from Q, i.e., g: R→Q, and a region map taking values from L, i.e., m: R→L.

If input DW-MRI image data is defined as g, and co-aligned to a training database of kidney image data, a map m may be described with a joint probability model:

$$P(g,m)=P(g|m)P(m), \quad (21)$$

which combines a conditional distribution of images given the map P(g|m) and an unconditional probability distribution of maps $P(m)=P_s(m)P_V(m)$, where $P_s(m)$ denotes an adaptive shape prior, and $P_V(m)$ is a Gibbs probability distribution with potentials V, which specifies an MGRF model of m.

To reduce the variability across subjects (i.e., image data from different patients) and to enhance the segmentation accuracy, embodiments of the invention may employ an adaptive shape model of an expected kidney shape. To create an expected kidney shape, a training set of kidney image data collected from different subjects may be co-aligned using the 3D B-splines based transformation described above. Probabilistic shape priors may be spatially variant independent random fields of region labels described by the following equations:

$$P_s(m)=\Pi_{(x,y,z)\in R}\, p_{s:x,y,z}(m_{x,y,z}) \quad (22)$$

where $P_{s:x,y,z}(1)$ corresponds to a voxel-wise empirical probability for each label l∈L For input DW-MRI data to be segmented, a shape prior may be constructed by an adaptive process guided by the visual appearance features of the input image data, where such adaptive process may be trained with previously segmented data sets (e.g., training sets) that may be used to create probabilistic maps for kidney object/background labels. Consistent with embodiments of the invention, for a kidney to be classified, corresponding DW-MRI data to be segmented may be first co-aligned with one of the training sets used to create the prior kidney shapes. Then, an appearance-guided shape prior may be estimated and updated based on an analysis of the aligned image data.

Furthermore, some embodiments of the invention may determine a second-order appearance model that may be used for segmentation. Generally, the second-order appearance model may incorporate three dimensional pair-wise interactions between region labels into a model, where the interactions may be estimated using a Potts model (i.e., an MGRF model with a nearest 26-neighbors of voxels) and analytic bi-valued Gibbs potentials that depend only on whether nearest pairs of labels are equal or not. A second-order appearance model may be determined based at least in part on the following equations:

$f_{eq}(m)$ denotes the relative frequency of equal labels in the neighboring voxel pairs:

$$((x,y,z),(x+\xi,y+\eta,z+\zeta))\in R^2; (\xi,\eta,\zeta)\in\{(\pm1,0,0),(0,\pm1,0),\\(\pm1,\pm1,0),(\pm1,0,\pm1),(0,\pm1,\pm1),(\pm1,\pm1,\pm1)\}, \quad (23)$$

where the initial map results in an analytical maximum likelihood estimates of the potentials $\upsilon_{eq}=-\upsilon_{ne}\approx 2f_{eq}(m)-1$, and computing voxel-wise probabilities corresponds to $P_{V_{x,y,z}}(l); l\in L$.

In addition, some embodiments of the invention may determine a first-order appearance model that may be used for segmentation. Generally, the first-order appearance model may comprise a linear combination of discrete Gaussians (LCDG) with positive and negative discrete Gaussian components. The first-order appearance model generally separates mixed empirical one dimensional distribution of DW-MRI voxel intensities into two distinct components, associated with each label. As will be appreciated, the first-order appearance model yields an initial region map that is formed by the voxel-wise classification of the image gray values.

Consistent with embodiments of the invention, the appearance-based shape model, the second-order appearance model, and the first-order appearance model may be integrated into a joint MGRF model to provide voxel-wise guidance of the level-set. A magnitude and direction of contour evolution at a voxel $u=(x, y, z)$ may be determined based on the following equations:

$$u_{md} = \begin{cases} -\kappa P_{ob:u}, & \text{if } P_{ob:u} > P_{bg:u} \\ \kappa P_{bg:u}, & \text{if } P_{bg:u} > P_{ob:u} \end{cases} \quad (24)$$

where
κ corresponds to a mean contour curvature, $P_{ob:u}$ corresponds to the joint MGRF probability for a kidney object, and $P_{bg:u}$ corresponds to the joint MGRF probability for background.

$$P_{ob:u} = \frac{\Omega_{ob:u}}{\Omega_{ob:u} + \Omega_{ob:u}}, \quad (25)$$

$P_{bg:u}=1-P_{ob:u}$, where
$\Omega_{ob:u}=p(q|1)P_{V:u}(1)P_{sp:u}(1)$,
$\Omega_{bg:u}=p(q|0)(1-P_{V:u}(1))(1-P_{sp:u}(1))$,
p(q|l) denotes the voxel-wise probability of the intensity $q\in Q$ for the LCDG model of the kidney (l=1) or background (l=0) appearance.

Based on the segmented image data that corresponds to the kidney object, the computer 30 may determine diffusion parameters (block 460). In some embodiments, the computer 30 may determine an apparent diffusion coefficient (ADC) for the kidney object of the segmented image data, where the ADC may be determined based at least in part on the following equation:

$$ADC = \frac{1}{b_0 - b} \ln\left(\frac{S_b}{S_0}\right), \quad (26)$$

where $S_0$ corresponds to DW-MRI data acquired at $b_0$ and $S_b$ corresponds to a given b-value.

Figure 13:
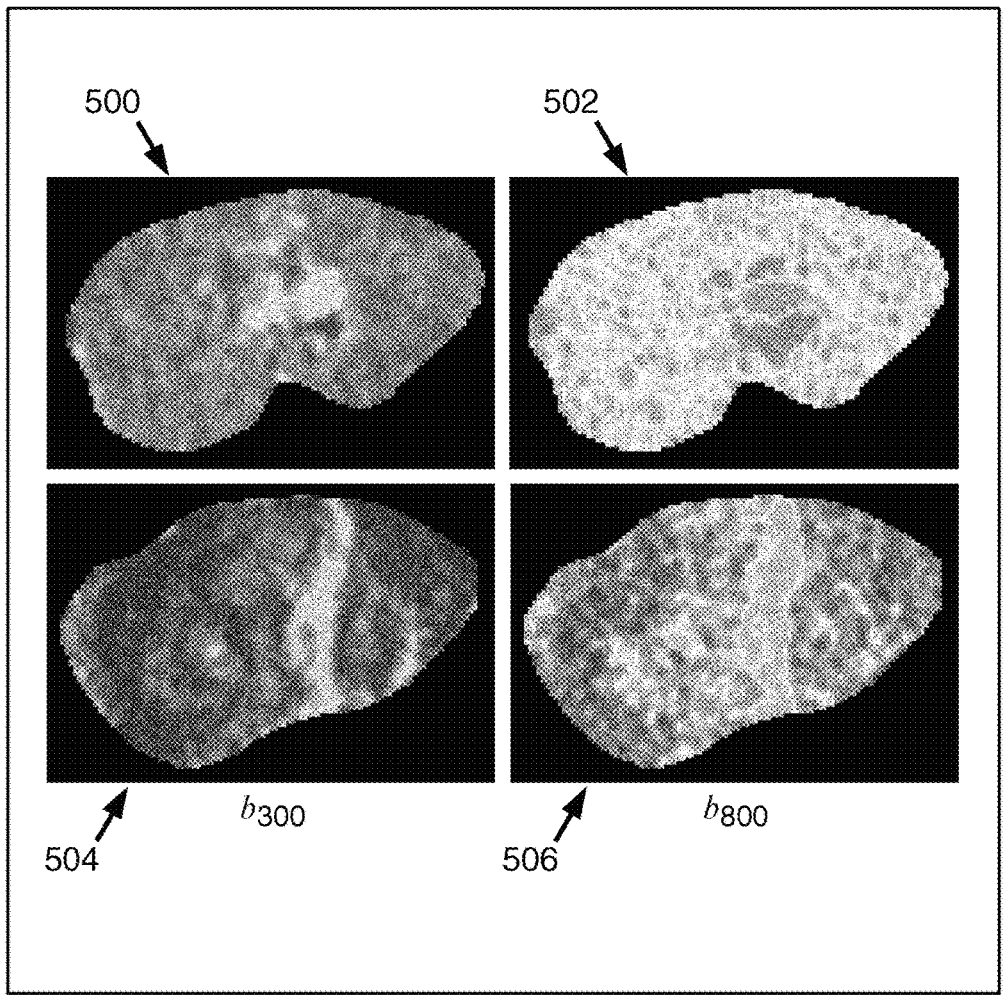
FIG. 13 provides a diagrammatic illustration of image data and a color-coded kidney that may be processed by the computer of FIG. 2.

The computer 30 may classify the kidney corresponding to the image data based at least in part on the diffusion parameters (block 462). In general, the computer 30 may compare the ADC determined for different b-values to ADC values determined for a training set. The computer 30 may perform a $k_n$-nearest neighbor classifier and a leave-one-subject out analysis process to classify the kidney as a rejection or non-rejection case. FIG. 13 provides a diagrammatic illustration of a cross-sectional voxel-wise parametric-maps constructed from DW-MRI image data collected at different b-values. In this example, a first set of image data corresponds to DW-MRI image data collected for a non-rejection case at b=300 s/mm² 500 and the non-rejection case at b=800 s/mm² 502. A second set of image data corresponds to DW-MRI image data collected for a rejection case at b=300 s/mm² 504 and b=800 s/mm² 506.

Therefore, embodiments of the invention may be used for the classification of acute rejection versus non-rejection status of kidney transplants. In some embodiments, two-dimensional dynamic contrast-enhanced magnetic resonance imaging data associated with a kidney may be processed and analyzed. In some embodiments, four-dimensional diffusion weighted magnetic resonance imaging data associated with a kidney may be processed an analyzed. In general, kidney objects may be segmented from adjacent structures with a level set deformable boundary guided by a stochastic speed function that accounts for a fourth-order Markov-Gibbs random field model of the kidney/background shape and appearance. A Laplace-based nonrigid registration approach may be used to account for local deformations caused by physiological effects. For example, the target kidney object may be deformed over closed, substantially equi-spaced contours (iso-contours) to closely match a reference object. In some embodiments, renal cortex image data may be segmented from kidney image data, as the renal cortex is most affected by rejection. To characterize rejection, one or more features may be determined, including for example, perfusion may be estimated from contrast agent kinetics using empirical indexes. For example, transient phase indexes (peak signal intensity, time-to-peak, and initial up-slope), and a steady-phase index defined as the average signal change during the slowly varying tissue phase of agent transit may be used to estimate one or more features. A $k_n$-nearest neighbor classifier may distinguish between acute rejection and non-rejection for classification.

Experimental results in 50 subjects, using a combinatoric $k_n$-classifier, correctly classified 92% of training subjects, 100% of the test subjects, and yielded an area under a receiver operating characteristics (ROC) curve that approached an ideal value. Therefore, embodiments of the invention may be utilized as a reliable non-invasive diagnostic tool. In other experimental results, of 35 subjects, embodiments described herein correctly classified 91.5% of the test subjects. Additional details regarding experimental results may be found in the incorporated description materials [1], [2], [3], and [4].

In general, the routines executed to implement the embodiments of the invention, whether implemented as part of an operating system or a specific application, component, program, object, module or sequence of instructions, or even a subset thereof, will be referred to herein as "computer program code," or simply "program code." Program code typically comprises one or more instructions that are resident at various times in various memory and storage devices in a computer, and that, when read and executed by one or more processors in a computer, cause that computer to perform the steps necessary to execute steps or elements embodying the various aspects of the invention. Moreover, while the invention has and hereinafter will be described in the context of fully functioning computers and computer systems, those skilled in the art will appreciate that the various embodiments of the invention are capable of being distributed as a program product in a variety of forms, and that the invention applies equally regardless of the particular type of computer readable media used to actually carry out the distribution. Examples of computer readable storage media include but are not limited to physical, tangible storage media such as volatile and non-volatile memory devices, floppy and other removable disks, hard disk drives, magnetic tape, optical disks (e.g., CD-ROMs, DVDs, etc.), among others.

In addition, various program code described herein may be identified based upon the application within which it is implemented in a specific embodiment of the invention. However, it should be appreciated that any particular program nomenclature that follows is used merely for convenience, and thus the invention should not be limited to use solely in any specific application identified and/or implied by such nomenclature. Furthermore, given the typically endless number of manners in which computer programs may be organized into routines, procedures, methods, modules, objects, and the like, as well as the various manners in which program functionality may be allocated among various software layers that are resident within a typical computer (e.g., operating systems, libraries, API's, applications, applets, etc.), it should be appreciated that the invention is not limited to the specific organization and allocation of program functionality described herein.

Embodiments of the invention therefore analyze and classify a kidney by analyzing medical image data associated with the kidney. In some embodiments, automated classification of a kidney using the present invention may provide significant benefits over conventional methods, including for example, improved classification speed and accuracy, and non-invasive classification as compared to a biopsy.

In addition, it will be appreciated that the invention may have applicability in terms of classifying other anatomical structures, including other organs. Furthermore, it will be appreciated that some embodiments of the invention may evaluate a non-transplanted kidney for various purposes by using a different learned model.

Other modifications will be apparent to one of ordinary skill in the art. Therefore, the invention lies in the claims hereinafter appended.

What is claimed is:

1. A method for classifying a kidney, the method comprising:
    receiving image data associated with an abdomen scan that includes image data of a kidney;
    segmenting, with at least one processor of a computer, kidney image data associated with the kidney from other image data of the abdomen scan based at least in part on a weighted probabilistic shape associated with the kidney and uses a two level joint Markov-Gibbs random field probabilistic model associated with the kidney;
    registering, with the at least one processor, at least one iso-contour of the kidney image data by identifying the at least one iso-contour of the kidney image data with a Laplace equation to determine corresponding contours in each of a plurality of time slices of the kidney image data to thereby compensate for kidney motion across the plurality of time slices of the kidney image data;
    segmenting, with the at least one processor, renal cortex image data associated with a renal cortex of the kidney from the kidney image data based at least in part on the at least one iso-contour; and
    classifying the kidney as one of an acutely rejected transplant or a non-rejected transplant by analyzing at least one feature determined from the renal cortex image data using a learned model associated with the at least one feature.

2. The method of claim 1, wherein segmenting image data of the renal cortex from the kidney image data is based at least in part on intensity and spatial information of pixels of the kidney image data.

3. The method of claim 1, wherein classifying the kidney as one of an acutely rejected transplant or a non-rejected transplant by analyzing at least one feature identified in the renal cortex image data using a learned model associated with the at least one feature is based at least in part on a renal perfusion intensity curve.

4. The method of claim 1, wherein the at least one feature comprises perfusion values, the method further comprising:
    determining the perfusion values based at least in part on a signal intensity determined from the renal cortex image data.

5. The method of claim 1, further comprising:
    determining Gibbs potentials for the kidney image data, wherein the kidney image data is segmented from the other image data of the abdomen scan based at least in part on the Gibbs potentials.

6. The method of claim 1, wherein the image data includes a time series of images, the method further comprising:
    determining a speed function associated with a level-set evolution over the time series of images,
    wherein the kidney image data is segmented from the other image data based at least in part on the speed function.

7. The method of claim 1, wherein registering at least one iso-contour of the kidney image data further comprises:
    generating at least one distance map for the kidney image data by determining a minimum Euclidean distance for inner points of a kidney object of the kidney image data to a boundary of the kidney object,
    wherein the at least one iso-contour of the kidney image data is registered based at least in part on the at least one distance map.

8. The method of claim 1, further comprising:
    determining average intensities of the renal cortex image data over a time series of the image data;
    characterizing perfusion of the kidney based at least in part on the average intensities of the renal cortex image data, wherein the kidney is classified based at least in part on the perfusion characterization of the kidney.

9. The method of claim 1, wherein the at least one feature determined from the renal cortex image data is normalized based at least in part on a corresponding feature from the other image data.

10. The method of claim 9, wherein the corresponding feature from the other image data is a body wall muscle.

11. A system, comprising:
    at least one data processor;
    at least one memory; and
    program code stored on the at least one memory and configured to be executed by the at least one processor to cause the at least one processor to:
    receive image data associated with an abdomen scan that includes image data of a kidney;
    segment kidney image data associated with the kidney from other image data of the abdomen scan based at least in part on a weighted probabilistic shape associated with the kidney and uses a two level joint Markov-Gibbs random field probabilistic model associated with the kidney;

register at least one iso-contour of the kidney image data by identifying the at least one iso-contour of the kidney image data with a Laplace equation to determine corresponding contours in each of a plurality of time slices of the kidney image data to thereby compensate for kidney motion across the plurality of time slices of the kidney image data;

segment renal cortex image data associated with a renal cortex of the kidney from the kidney image data based at least in part on the at least one iso-contour; and classify the kidney as one of an acutely rejected transplant or a non-rejected transplant by analyzing at least one feature determined from the renal cortex image data using a learned model associated with the at least one feature.

12. The system of claim 11, wherein the renal cortex image data is segmented from the kidney image data based at least in part on intensity and spatial information of pixels of the kidney image data.

13. The system of claim 11, wherein the at least one feature comprises perfusion values, and the program code is further configured upon execution to cause the at least one processor to:

determine the perfusion values based at least in part on a signal intensity determined from the renal cortex image data.

14. The system of claim 11, wherein the program code is further configured upon execution to cause the at least one processor to:

determine Gibbs potentials for the kidney image data,
wherein the kidney image data is segmented from the other image data of the abdomen scan based at least in part on the Gibbs potentials.

15. The system of claim 11, wherein the image data includes a time series of images, and the program code is further configured upon execution to cause the at least one processor to:

determine a speed function associated with a level set evolution over the time series of images,
wherein the kidney image data is segmented from the other image data based at least in part on the speed function.

16. The system of claim 11, wherein the at least one iso-contour of the kidney image data is further registered by:

generating a distance map for the kidney image data by determining a minimum Euclidean distance for inner points of a kidney object of the kidney image data to a boundary of the kidney object,
wherein the at least one iso-contour of the kidney image data is registered based at least in part on the distance map.

17. The system of claim 11, wherein the program code is further configured upon execution to cause the at least one processor to:

determine average intensities of the renal cortex image data over a time series of the image data;
characterize perfusion of the kidney based at least in part on the average intensities of the cortex image data,
wherein the kidney is classified based at least in part on the perfusion characterization of the kidney.

* * * * *